US00PP32374P2

(12) United States Plant Patent
Schmidt

(10) Patent No.: US PP32,374 P2
(45) Date of Patent: Oct. 20, 2020

(54) ***SCHIZACHYRIUM* PLANT NAMED 'HA HA TONKA'**

(50) Latin Name: *Schizachyrium scoparium*
Varietal Denomination: Ha Ha Tonka

(71) Applicant: Cassian Schmidt, Weinheim (DE)

(72) Inventor: Cassian Schmidt, Weinheim (DE)

(73) Assignee: Future Plants Licentie B.V., Lisserbroek (NL)

( * ) Notice: Subject to any disclaimer, the term of this patent is extended or adjusted under 35 U.S.C. 154(b) by 0 days.

(21) Appl. No.: 16/602,999

(22) Filed: Jan. 13, 2020

(51) Int. Cl.
*A01H 5/12* (2018.01)
*A01H 6/46* (2018.01)

(52) U.S. Cl.
USPC ..... Plt./384
CPC ..... *A01H 6/46* (2018.05)

(58) Field of Classification Search
USPC ..... Plt./384
CPC ..... A01H 6/46; A01H 5/12
See application file for complete search history.

*Primary Examiner* — Keith O. Robinson
(74) *Attorney, Agent, or Firm* — C. A. Whealy

(57) ABSTRACT

A new and distinct cultivar of *Schizachyrium* plant named 'Ha Ha Tonka', characterized by its upright, strong and rigid plant habit; moderately vigorous to vigorous growth habit and moderately rapid growth rate; acicular medium green and greyed orange-colored leaves that are densely pubescent; and good garden performance.

2 Drawing Sheets

Figure 1:
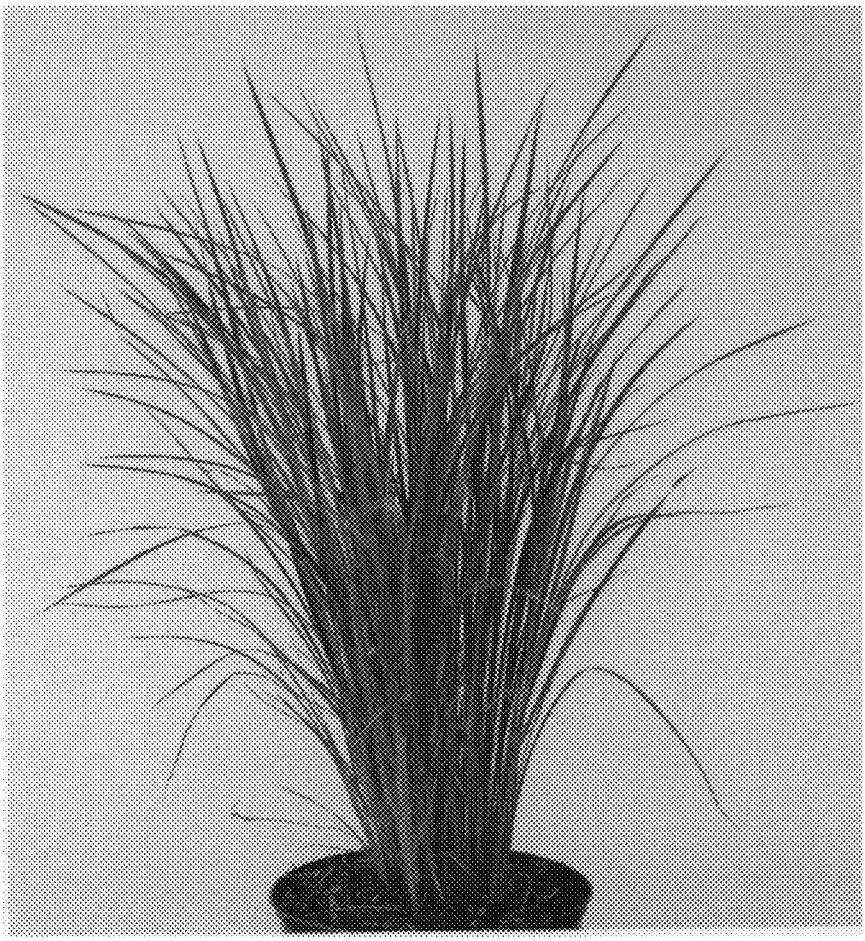

Botanical designation: *Schizachyrium scoparium*.
Cultivar denomination: 'HA HA TONKA'.

BACKGROUND OF THE INVENTION

The present invention relates to a new and distinct cultivar of *Schizachyrium* plant, botanically known as *Schizachyrium scoparium*, commonly referred to as Blue Stem or Bunchgrass and hereinafter referred to by the name 'Ha Ha Tonka'.

The new *Schizachyrium* plant originated from an open-pollination during the summer of 2015 in Weinheim, Germany, of an unidentified proprietary selection of *Schizachyrium scoparium*, not patented, as the female, or seed, parent with an unknown selection of *Schizachyrium scoparium* as the male, or pollen, parent. The new *Schizachyrium* plant was discovered and selected by the Inventor as a single plant from within the progeny of the stated open-pollination in a controlled outdoor environment in Weinheim, Germany in September, 2016.

Asexual reproduction of the new *Schizachyrium* plant by divisions in a controlled environment in Weinheim, Germany since September, 2016 has shown that the unique features of this new *Schizachyrium* plant are stable and reproduced true to type in successive generations.

SUMMARY OF THE INVENTION

Plants of the new *Schizachyrium* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Ha Ha Tonka'. These characteristics in combination distinguish 'Ha Ha Tonka' as a new and distinct *Schizachyrium* plant:

1. Upright, strong and rigid plant habit.
2. Moderately vigorous to vigorous growth habit and moderately rapid growth rate.
3. Acicular medium green and greyed orange-colored leaves that are densely pubescent.
4. Good garden performance.

Plants of the new *Schizachyrium* differ primarily from plants of the female parent selection in growth habit as plants of the new *Schizachyrium* are more vigorous than plants of the female parent selection.

Plants of the new *Schizachyrium* can be compared to plants of *Schizachyrium scoparium* 'The Blues', not patented. Plants of the new *Schizachyrium* differ primarily from plants of 'The Blues' in the following characteristics:

1. Plants of the new *Schizachyrium* are taller than plants of 'The Blues'.
2. Leaves of plants of the new *Schizachyrium* are more densely pubescent than leaves of plants of 'The Blues'.
3. Leaves of plants of the new *Schizachyrium* are more greyed orange in color than leaves of plants of 'The Blues'.

Plants of the new *Schizachyrium* can also be compared to plants of *Schizachyrium scoparium* 'MinnblueA', disclosed in U.S. Plant Pat. No. 17,310. Plants of the new *Schizachyrium* differ primarily from plants of 'MinnblueA' in the following characteristics:

1. Plants of the new *Schizachyrium* are slightly shorter than plants of 'MinnblueA'.
2. Plants of the new *Schizachyrium* are stronger and more rigid than plants of 'MinnblueA'.
3. Leaves of plants of the new *Schizachyrium* are more densely pubescent than leaves of plants of 'MinnblueA'.

BRIEF DESCRIPTION OF THE PHOTOGRAPHS

The accompanying colored photographs illustrate the overall appearance of the new *Schizachyrium* plant showing the colors as true as it is reasonably possible to obtain in colored reproductions of this type. Colors in the photographs may differ slightly from the color values cited in the detailed botanical description which accurately describe the colors of the new *Schizachyrium* plant.

The photograph on the first sheet (FIG. 1 of 2) is a side perspective view of typical plant of 'Ha Ha Tonka' grown in a container.

Figure 2:
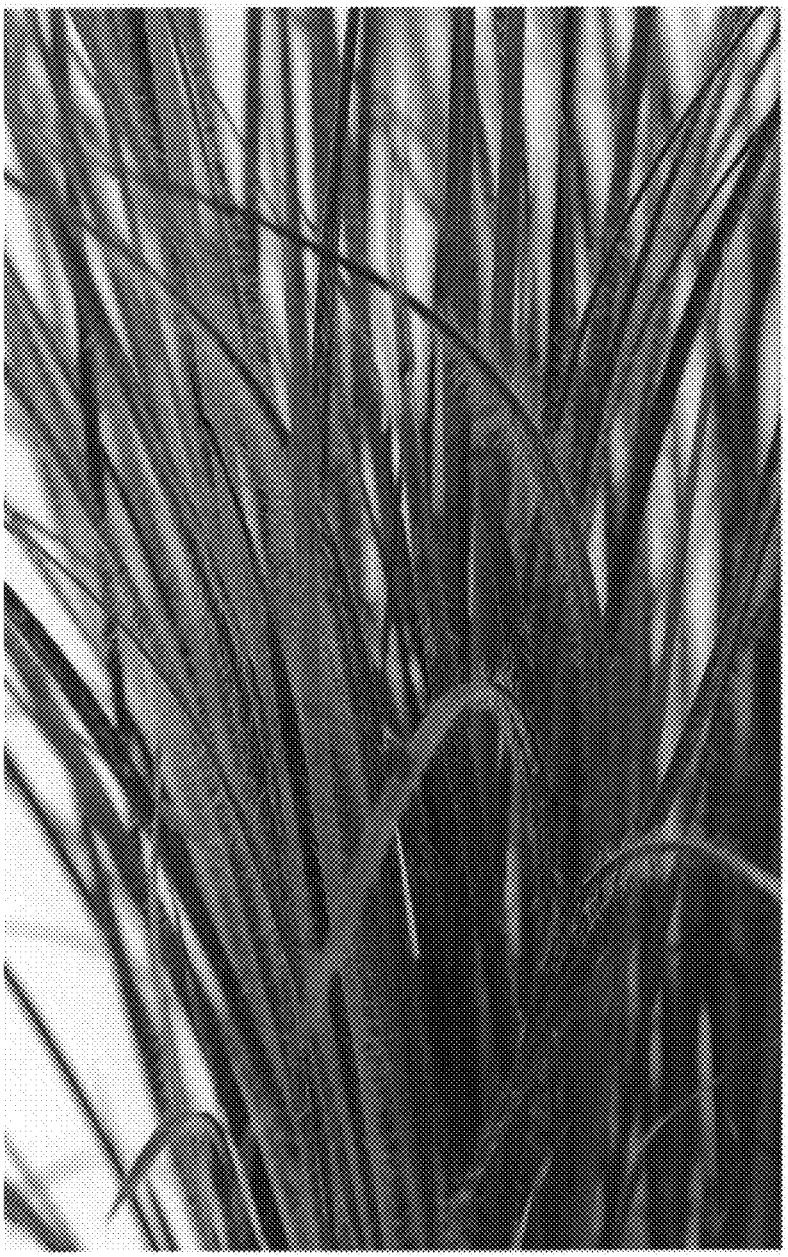

The photograph on the second sheet (FIG. 2 of 2) is a close-up view of typical leaves of 'Ha Ha Tonka'.

DETAILED BOTANICAL DESCRIPTION

The aforementioned photographs and following observations, measurements and values describe plants grown during the summer in 16.7-cm containers in an outdoor nursery in Lisserbroek, The Netherlands and under cultural practices typical of commercial *Schizachyrium* production. During the production of the plants, day temperatures ranged from 18° C. to 35° C. and night temperatures ranged from 10° C. to 22° C. Plants were one year old when the photographs and description were taken. In the following description, color references are made to The Royal Horticultural Society Colour Chart, 2015 Edition, except where general terms of ordinary dictionary significance are used.

Botanical classification: *Schizachyrium scoparium* 'Ha Ha Tonka'.

Parentage:

*Female, or seed, parent*.—Unidentified proprietary selection of *Schizachyrium scoparium*, not patented.

*Male, or pollen, parent*.—Unknown selection of *Schizachyrium scoparium*, not patented.

Propagation:

*Type*.—By divisions.

*Time to produce a rooted young plant, summer*.—About twelve weeks at ambient temperatures about 20° C.

*Root description*.—Fine; tough; typically yellowish white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Herbaceous perennial typically grown as an ornamental grass; upright, strong and rigid plant habit, overall plant shape, obovate; moderately vigorous to vigorous growth habit and moderate growth rate.

*Plant height*.—About 46.5 cm.

*Plant width* (*spread*).—About 45 cm.

Leaf description:

*Arrangement*.—Leaves are arranged in basal clumps with about six leaves per clump and about 45 basal clumps per plant; leaves sheathing and sessile.

*Length*.—About 46.5 cm.

*Width*.—About 3.5 mm.

*Shape*.—Acicular, moderately carinate and slightly curved.

*Apex*.—Long and narrowly acuminate.

*Base*.—Sheathing.

*Margin*.—Entire, not undulate.

*Texture and luster, upper and lower surfaces*.—Densely pubescent, not rugose; matte.

*Venation pattern*.—Parallel.

*Color*.—Developing leaves, upper surface: Close to N144C. Developing leaves, lower surface: Close to N144B. Fully developed leaves, upper surface: Close to 137A and 137B; distally, close to 174A to 174B and 177B; venation, close to 137C. Fully developed leaves, lower surface: Close to 137B; distally, close to 174A and 177B; venation, close to 137B.

*Leaf sheaths*.—Length: About 11.9 cm. Diameter: About 3 mm. Color, upper and lower surfaces: Close to 144A; proximally, close to 146D.

Flower description: To date, flower development has not been observed on plants of the new *Schizachyrium*.

Pathogen & pest resistance: Plants of the new *Schizachyrium* have not been observed to be resistant to pathogens and pests common to *Schizachyrium* plants.

Garden performance: Plants of the new *Schizachyrium* have exhibited good tolerance to rain, wind and temperatures ranging from about −23° C. to about 40° C. and to be suitable for USDA Hardiness Zones 5 to 10.

It is claimed:

1. A new and distinct *Schizachyrium* plant named 'Ha Ha Tonka' as illustrated and described.

* * * * *